(12) United States Patent
Hendricks

(10) Patent No.: US 10,667,953 B2
(45) Date of Patent: Jun. 2, 2020

(54) INSTRUMENT FOR EXAMINATION OF EAR AND REMOVAL OF EAR WAX

(71) Applicant: Larry A. Hendricks, LaMoure, ND (US)

(72) Inventor: Larry A. Hendricks, LaMoure, ND (US)

(*) Notice: Subject to any disclaimer, the term of this patent is extended or adjusted under 35 U.S.C. 154(b) by 0 days.

(21) Appl. No.: 16/058,539

(22) Filed: Aug. 8, 2018

(65) Prior Publication Data

US 2019/0046359 A1   Feb. 14, 2019

Related U.S. Application Data

(60) Provisional application No. 62/542,564, filed on Aug. 8, 2017.

(51) Int. Cl.
| *A61F 11/00* | (2006.01) |
| *A61B 1/00* | (2006.01) |
| *A61B 1/227* | (2006.01) |
| *A61B 1/32* | (2006.01) |

(52) U.S. Cl.
CPC ........ *A61F 11/006* (2013.01); *A61B 1/00087* (2013.01); *A61B 1/00135* (2013.01); *A61B 1/227* (2013.01); *A61B 1/32* (2013.01)

(58) Field of Classification Search
CPC .......... A61B 1/227; A61F 11/00; A61F 11/06; A61F 11/002
USPC ........................................ 600/184, 200, 235
See application file for complete search history.

(56) References Cited

U.S. PATENT DOCUMENTS

| 672,317 | A |  | 4/1901 | Dow |
| 2,184,414 | A |  | 12/1939 | Dittmer |
| 4,006,738 | A |  | 2/1977 | Moore et al. |
| 4,785,796 | A | * | 11/1988 | Mattson ................. A61B 1/227 362/109 |
| D333,702 | S | * | 3/1993 | Hufman ....................... D24/135 |
| 5,509,921 | A |  | 4/1996 | Karell |
| 2014/0171743 | A1 | * | 6/2014 | Heine ................ A61B 1/00142 600/200 |
| 2016/0367404 | A1 |  | 12/2016 | Shomo |

FOREIGN PATENT DOCUMENTS

| EP | 0367855 A1 | 5/1990 |
| JP | 2003079573 A | 3/2003 |
| WO | WO2005/016117 A2 | 2/2005 |

OTHER PUBLICATIONS

International Search Report and Written Opinion from PCT Application Serial No. PCT/US2018/045792, dated Nov. 19, 2018, 11 pages.

* cited by examiner

*Primary Examiner* — Julianna N Harvey
*Assistant Examiner* — Christina Negrellirodriguez
(74) *Attorney, Agent, or Firm* — Kinney & Lange, P. A.

(57) ABSTRACT

An instrument for use with an otoscope to examine an ear and remove cerumen (i.e., ear wax) from an ear canal includes a speculum having a channel extending between a tip and a rear with the tip having a first side and a second side opposite the first side and a curette having a through hole a first end connected to the first side of the speculum, and a second end connected to the second side of the speculum.

19 Claims, 3 Drawing Sheets

INSTRUMENT FOR EXAMINATION OF EAR AND REMOVAL OF EAR WAX

CROSS-REFERENCE TO RELATED APPLICATION(S)

This application claims the benefit of U.S. Provisional Application No. 62/542,564 filed Aug. 8, 2017, for "Instrument for Examination of Ear and Removal of Ear Wax" by L. Hendricks.

FIELD OF THE INVENTION

The present invention relates to removal of cerumen (i.e., ear wax) and, in particular, an instrument that is inserted into the ear canal to manually remove ear wax.

BACKGROUND

When an ear is examined by a medical professional, the medical professional must use one hand to pull the external portion of the ear backwards to straighten the curved ear canal in order to visualize the tympanic membrane (i.e., the ear drum). The medical professional then uses the other hand to accomplish the task of examining the ear. This examination often requires a magnified light source to illuminate the ear canal and an otoscope with an appropriately sized ear speculum, which can be a hollow, frustoconical apparatus through which a medical professional can look to examine the ear canal. If removal of ear wax within the ear canal is needed, the medical professional also needs a separate apparatus (such as an ear curette), which can be a hook that is inserted into the ear canal to scoop and remove the ear wax from the ear canal.

Often times, medical professionals elect to leave the ear wax within the ear canal because removal is burdensome and time consuming due to the need for the medical professional to hold the external portion of the ear backwards, hold the ear speculum in place, and also utilize the ear curette to remove the ear wax. During such a procedure, the medical professional has difficulty performing the three tasks with two hands.

SUMMARY

An instrument includes a speculum having a channel extending between a tip and a rear with the tip having a first side and a second side opposite the first side and a curette having a through hole, a first end connected to the first side of the speculum, and a second end connected to the second side of the speculum.

A system for use with an otoscope to examine an ear and remove cerumen from an ear canal includes a speculum that is a hollow frustoconical shape with a tip, a rear, a first side, a second side, and a channel extending from the rear to the tip. The system also includes a loop with one end connected to the first side and another end connected to the second side with the loop having a through hole.

DETAILED DESCRIPTION

An ear speculum and curette instrument for both the examination (i.e., viewing) of the ear and removal of cerumen (i.e., ear wax) is disclosed herein that is able to be utilized with a conventional otoscope. The instrument includes an ear speculum with a channel through which light provided by the otoscope can pass and through which a medical professional can view internal components of a patient's ear, such as an ear canal and/or ear drum. The instrument also includes an ear curette (also referred to as a loop in this disclosure) on a tip of the speculum that can remove ear wax from the ear canal. The instrument provides a single apparatus/instrument that allows the medical professional to both examine/view the ear and scoop and remove ear wax from the ear canal. Without the disclosed speculum and curette instrument, two or more instruments would be needed to perform the same tasks. Once examination and removal of the ear wax is complete, the instrument can be disengaged from the otoscope and discarded as the instrument can be replaceable/disposable after a single use or multiple uses. The instrument's utilization is wide ranging as the instrument is compatible with conventional otoscopes. The instrument is easy to use and increases the safety and comfort of the patient.

Figure 1A:
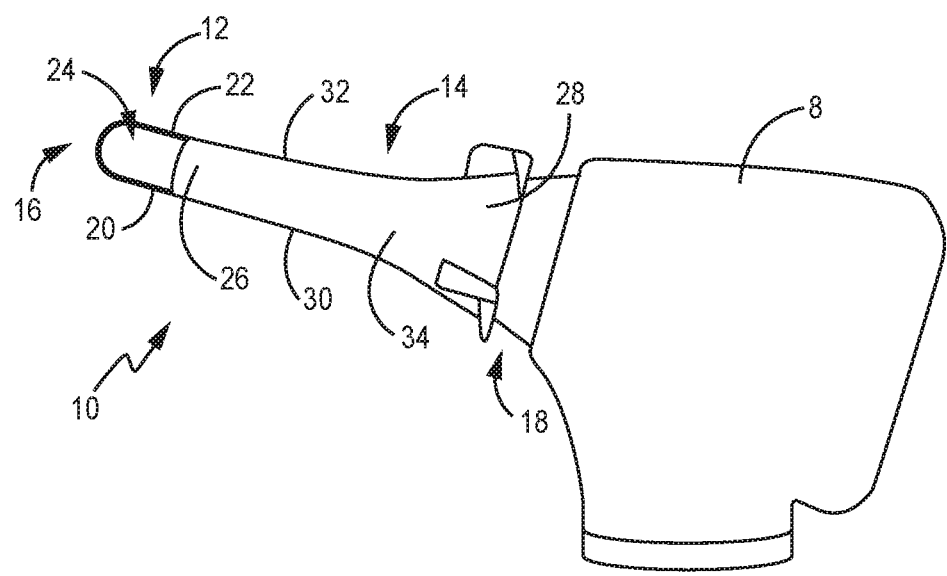
FIG. 1A is an ear speculum and curette instrument located on an otoscope.
Figure 1B:
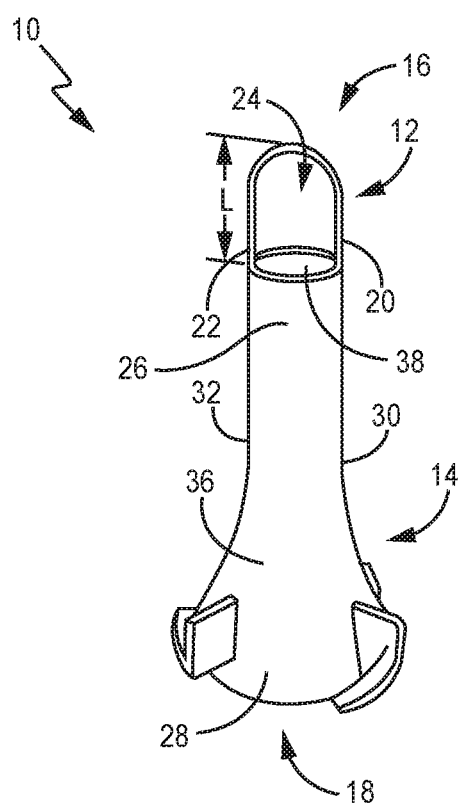
FIG. 1B is a side perspective view of the ear speculum and curette instrument.
Figure 1C:
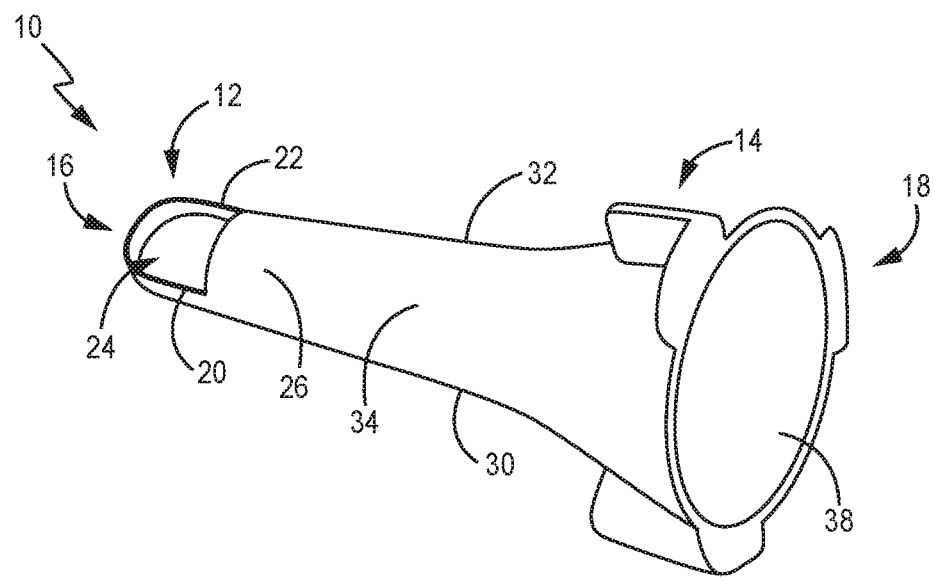
FIG. 1C is another side perspective view of the ear speculum and curette instrument.
Figure 1D:
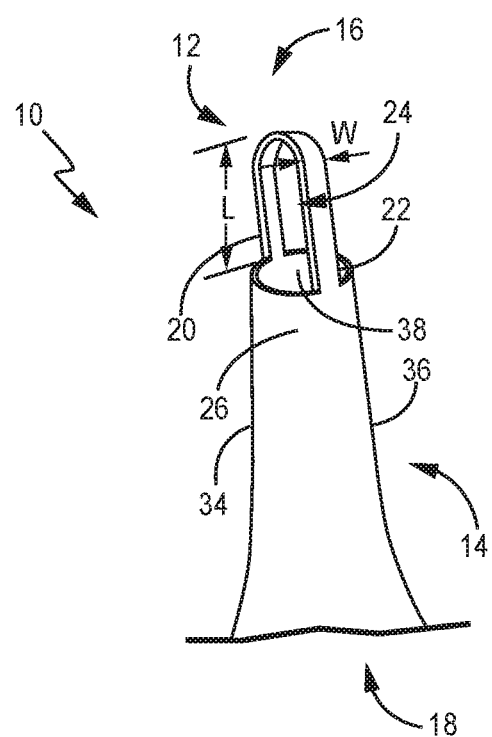
FIG. 1D is an enlarged top perspective view of the ear speculum and curette instrument.
Figure 1E:
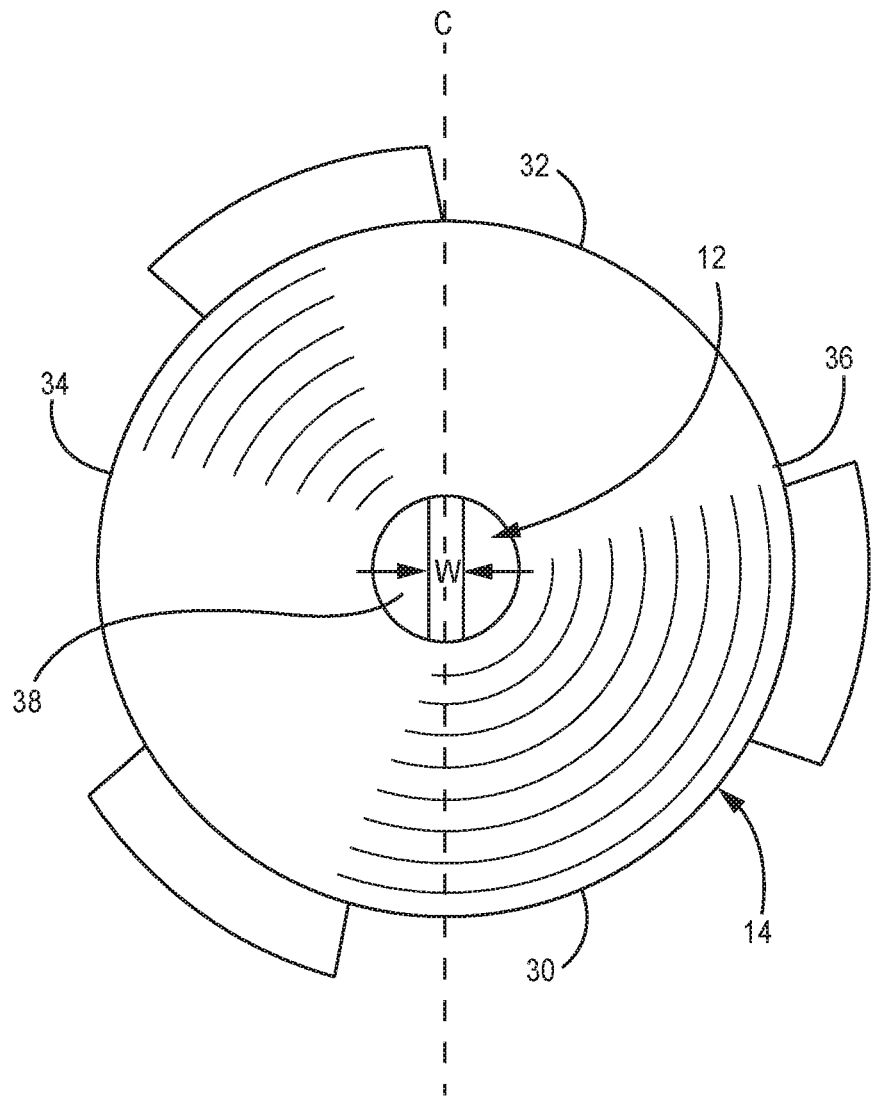
FIG. 1E is a rear perspective view of the ear speculum and curette instrument viewed through a channel of the speculum to see the curette.

FIG. 1A is ear speculum and curette instrument 10 engaged with/attached to otoscope 8, FIG. 1B is a side perspective view of instrument 10, FIG. 1C is another side perspective view of instrument 10, FIG. 1D is an enlarged top perspective view of instrument 10, and FIG. 1E is a rear perspective view of instrument 10 viewed through channel 38 of speculum 14 to see curette 12. Instrument 10 includes curette 12 and speculum 14. Curette 12 is at front 16 and speculum 14 is at rear 18. Curette 12 includes first attachment end 20, second attachment end 22, and through-hole 24. Speculum 14 includes tip 26, rear 28, first side 30, second side 32, top 34, bottom 36, and channel 38 extending completely through speculum 14 between tip 26 and rear 28. Speculum 14 can also include other features enabling instrument 10 to attach to and detach from otoscope 8.

Otoscope 8 is an instrument utilized by medical professionals that usually includes a handle and a light. The light is directed into the internal ear to examine the components of the ear. In this disclosure, otoscope 8 is a conventional otoscope, and otoscope 8 can include other features not expressly disclosed herein.

Instrument 10 is configured to be engageable/attachable to and disengageable/detachable from otoscope 8 and is configured to be utilized with any conventional otoscope. Instrument 10 can be one continuous and monolithic component (i.e., curette 12 and speculum 14 can be molded/formed to one another to be one continuous piece). Instrument 10 can be constructed from a variety of materials, such as any suitable plastic, polymer, composite, or metallic material. In one example, instrument 10 is constructed from a clear/transparent material. For example, instrument 10 can be constructed from polyolefin, polyvinylchloride, polycarbonates, acrylonitrile butadiene styrene, nylons, polyacetal, polyesters, polyether, polytetrafluoroethylene, polyimide, polyvinylidene fluoride, and/or their derivatives. As discussed below, the material used to construct curette 12 may be chosen to ensure curette 12 is flexible, semi-flexible, or rigid depending on design considerations and the need for curette 12 to either be flexible within the ear canal to bend to scoop ear wax and/or be rigid to withstand the stresses of scooping the ear wax. As discussed below, curette 12 can have a cross-sectional shape that is rectangular to allow for curette 12 to be both flexible enough to fit within the ear canal and rigid enough to scoop and remove the ear wax (i.e., curette 12 can be a flat, rectangular strip that is curved between first attachment end 20 and second attachment end 22).

Curette 12 can be a loop having first end 20 attached to first side 30 of tip 26 of speculum 14, a semi-oblong shape that turns 180 degrees to change direction to extend towards speculum 14, and second end 22 attached to second side 32 of tip 26 of speculum 14. While curette 12 is shown as having a semi-oblong shape, curette 12 can have other shapes, such as semi-circular, rectangular, oval, and triangular. As shown in FIG. 1D, width W of curette 12 is less than a width of speculum 14 at tip 26. In one example, width W of curette 12 is between 0.5 millimeters (0.02 inches) and 4.0 millimeters (0.16 inches). Further, as shown most easily in FIG. 1D, curette 12 has a substantially rectangular cross-sectional shape that allows curette 12 to bend under stress coming from front 16, first side 20, and second side 32 while being sufficiently rigid to withstand stresses from top 34 and/or bottom 36 to be able to scoop and remove ear wax within the ear canal (i.e., curette 12 can be a flat, rectangular strip that is curved between first attachment end 20 and second attachment end 22). In other words, curette 12 can have width W in a top-to-bottom direction (i.e., from top 34 to bottom 36) that is greater than a thickness in a side-to-side direction (i.e., from first side 30 to second side 32 at a point where curette 12 attaches to first side 30). For example, the cross section of curette 12 can have width W of 0.5 to 4.0 millimeters while having a side-to-side thickness of 0.1 millimeters or less. In another examples, the thickness of curette 12 can be between 0.25 millimeters (0.01 inches) and 2.5 millimeters (0.10 inches).

Curette 12 can also be configured to be positioned along central plane C (shown in FIG. 1E), which bisects and extends longitudinally along instrument 10, such that a view looking through channel 38 of speculum 14 to examine components of a patient's ear is not substantially obstructed by curette 12. In other words, curette 12 can bisect channel 38 at a location near tip 26 of speculum 14. Such a configuration allows for a medical professional to look around curette 12 to view the components of the ear. Curette 12 can extend beyond tip 26 of speculum 14 any distance sufficient to allow curette 12 to scoop and remove ear wax. For example, length L (shown in FIG. 1D) that curette 12 extends away from speculum 14 can be 0.64 centimeters (0.25 inches), 0.95 centimeters (0.375 inches), or 1.27 centimeters (0.5 inches).

Speculum 14 is at rear 18 of instrument 10. Speculum 14 includes tip 26 adjacent curette 12 and rear 28 opposite tip 26. Speculum 14 can include four sides (although speculum 14 does not need to have a quadrilateral cross section and, as shown in the disclosed embodiment, can have a circular cross section) with those sides being first side 30 across from second side 32 and top 34 across from bottom 36. While sides of speculum 14 are denoted as "top" and "bottom," top 34 does not need to be above bottom 36 and the orientation of the sides of speculum 14 can change depending on how instrument 10 is attached/engaged to otoscope 8. Channel 38 extends through speculum 14 from rear 28 to tip 26 to allow for a medical professional to look through speculum 14 to view the components of a patient's ear. Speculum 14 can have any shape that allows for insertion of tip 26 into a patient's ear canal while also allowing for attachment/engagement to otoscope 8. Speculum 14 in the disclosed example is a substantially hollow frustoconical shape (channel 38 forms the hollow portion) with tip 26 having a circular opening at which first end 20 and second end 22 of curette 12 connect to first side 30 and second side 32 of speculum 14, respectively. At rear 28, speculum 14 can be configured to engage with and disengage from otoscope 8 to allow for replacement of instrument 10 after a single use or multiple uses. Speculum 14 can be configured to be used to examine a patient's ear without otoscope 8 or in conjunction with other medical devices.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. An instrument comprising:
    a speculum having a channel extending between a tip and a rear with the tip having a first side, a second side opposite the first side, a top between the first side and the second side, and a bottom opposite the top, the channel forming a view path through the speculum; and
    a curette having a through hole, a first end connected to the first side of the speculum, and a second end connected to the second side of the speculum with the curette having a width extending in a top-to-bottom direction and a thickness in a first-side-to-second-side direction measured at a point where the first end connects to the first side of the speculum,
    wherein the curette is positioned to divide the channel into two parts such that the curette is viewable through the channel of the speculum but the channel is not obstructed by the curette,
    wherein the width of the curette is greater than the thickness of the curette.

2. The instrument of claim 1, wherein the curette has a width that is less than a width of the tip of the speculum.

3. The instrument of claim 2, wherein the width of the curette is between 0.5 millimeters (0.02 inches) and 4.0 millimeters (0.16 inches).

4. The instrument of claim 1, wherein the curette is a semi-oblong shape.

5. The instrument of claim 1, wherein the speculum is a hollow frustoconical shape.

6. The instrument of claim 1, wherein a length of the curette is 0.64 centimeters (0.25 inches).

7. The instrument of claim 1, wherein a length of the curette is 1.27 centimeters (0.5 inches).

8. The instrument of claim 1, wherein the speculum is able to be placed onto an otoscope.

9. The instrument of claim 1, wherein the curette is positioned along a central plane such that a view through the channel of the speculum is not obstructed by the curette.

10. The instrument of claim 1, wherein the curette has a substantially rectangular cross-sectional shape that allows the curette to bend under stress coming from a direction of the first end and the second end.

11. The instrument of claim 1, wherein the speculum and curette are one continuous and monolithic piece.

12. The instrument of claim 1, wherein the curette is able to fit within an ear canal of a patient to collect cerumen.

13. A system for use with an otoscope to examine an ear and remove cerumen from an ear canal, the system comprising:
   a speculum that is a hollow frustoconical shape with a tip, a rear, a first side, a second side, a top between the first side and the second side, a bottom opposite the top, and a channel extending from the rear to the tip; and
   a loop having a through hole, a first end connected to the first side of the speculum, and a second end connected to the second side of the speculum, the loop having a width extending in a top-to-bottom direction and a thickness in a first-side-to-second-side direction measured at a point where the first end connects to the first side of the speculum,
   wherein the width of the loop is greater than the thickness of the loop such that the loop has a substantially rectangular cross-sectional shape that allows the loop to bend under stress coming from a direction of the first side and the second side.

14. The system of claim 13, wherein the loop is positioned along a central plane to bisect the channel at the tip of the speculum.

15. The system of claim 13, wherein the loop is a semi-oblong shape extending between the first side and the second side of the speculum.

16. The system of claim 13, wherein the loop has a width that is less than a width of the tip of the speculum.

17. The system of claim 13, wherein the speculum is configured to snap onto the otoscope to be engageable and disengageable with the otoscope.

18. The system of claim 13, wherein the loop is configured to be inserted into the ear canal to remove cerumen while also allowing examination of the ear canal by viewing the ear canal through the channel in the speculum.

19. The system of claim 13, wherein the speculum and loop are constructed from a plastic material or combination of plastic materials.

* * * * *